(12) United States Patent
Hagiwara et al.

(10) Patent No.: US 11,795,424 B2
(45) Date of Patent: Oct. 24, 2023

(54) CELL CULTURE VESSEL, SAMPLE OBSERVATION CELL, AND CELL CULTURE METHOD

(71) Applicants: University Public Corporation Osaka, Osaka (JP); National University Corporation Kyushu Institute of Technology, Kitakyushu (JP)

(72) Inventors: Masaya Hagiwara, Sakai (JP); Tomohiro Kawahara, Kitakyushu (JP)

(73) Assignees: University Public Corporation Osaka, Osaka (JP); National University Corporation Kyushu Institute of Technology, Fukuoka (JP)

(*) Notice: Subject to any disclaimer, the term of this patent is extended or adjusted under 35 U.S.C. 154(b) by 915 days.

(21) Appl. No.: 16/484,937

(22) PCT Filed: Dec. 5, 2017

(86) PCT No.: PCT/JP2017/043675
§ 371 (c)(1),
(2) Date: Aug. 9, 2019

(87) PCT Pub. No.: WO2018/150689
PCT Pub. Date: Aug. 23, 2018

(65) Prior Publication Data
US 2020/0017814 A1      Jan. 16, 2020

(30) Foreign Application Priority Data
Feb. 15, 2017   (JP) .................. 2017-026036

(51) Int. Cl.
*C12M 1/00*   (2006.01)
*C12N 5/071*   (2010.01)

(52) U.S. Cl.
CPC ............ *C12M 23/22* (2013.01); *C12N 5/0602* (2013.01)

(58) Field of Classification Search
None
See application file for complete search history.

(56) References Cited

U.S. PATENT DOCUMENTS 3,554,433 A * 1/1971 Cardenaz ................. G01N 1/36
                                                                      229/235
2007/0003526 A1    1/2007 Hayashi
(Continued)

FOREIGN PATENT DOCUMENTS

JP     2009-213716 A        9/2009
JP     2017023049 A  *     2/2017
(Continued)

OTHER PUBLICATIONS

European Patent Office, Extended European Search Report issued in corresponding Application No. EP 17 89 6937, dated Nov. 19, 2020.
(Continued)

*Primary Examiner* — William H. Beisner
(74) *Attorney, Agent, or Firm* — Stites & Harbison, PLLC; Jeffrey A. Haeberlin

(57) ABSTRACT

The present invention provides a cell culture vessel/sample observation cell that is capable of culturing cells or cell tissue in three dimensions and allowing a three-dimensional structure of the cells or the cell tissue to be perceived easily. The cell culture vessel/sample observation cell according to the present invention for containing a culture gel in which the cells or the cell tissue is embedded, comprises a frame, at least one window bordered by the frame, and at least one projection projecting from the frame inwardly into the cell culture vessel/sample observation cell, wherein the at least one window is light-permeable and nutrient component-permeable and is placed in such a way as to allow for
(Continued)

multifaceted observation of the cells or the cell tissue, and the projection has a feature point to be placed at a position where the cells or the cell tissue as well as the feature point can be observed from the window.

10 Claims, 4 Drawing Sheets

(56) References Cited

U.S. PATENT DOCUMENTS

| | | |
|---|---|---|
| 2014/0113365 A1 | 4/2014 | Nagai et al. |
| 2014/0127746 A1* | 5/2014 | Kachur .................. B01L 3/508 |
| | | 435/40.52 |
| 2015/0065588 A1 | 3/2015 | Weinberger et al. |

FOREIGN PATENT DOCUMENTS

| | | |
|---|---|---|
| WO | 2004/084967 A1 | 6/2006 |
| WO | 2012/147878 A1 | 7/2014 |

OTHER PUBLICATIONS

Japan Patent Office, International Search Report issued in corresponding Application No. PCT/JP2017/043675, dated Mar. 6, 2018.

* cited by examiner

[Fig. 1]
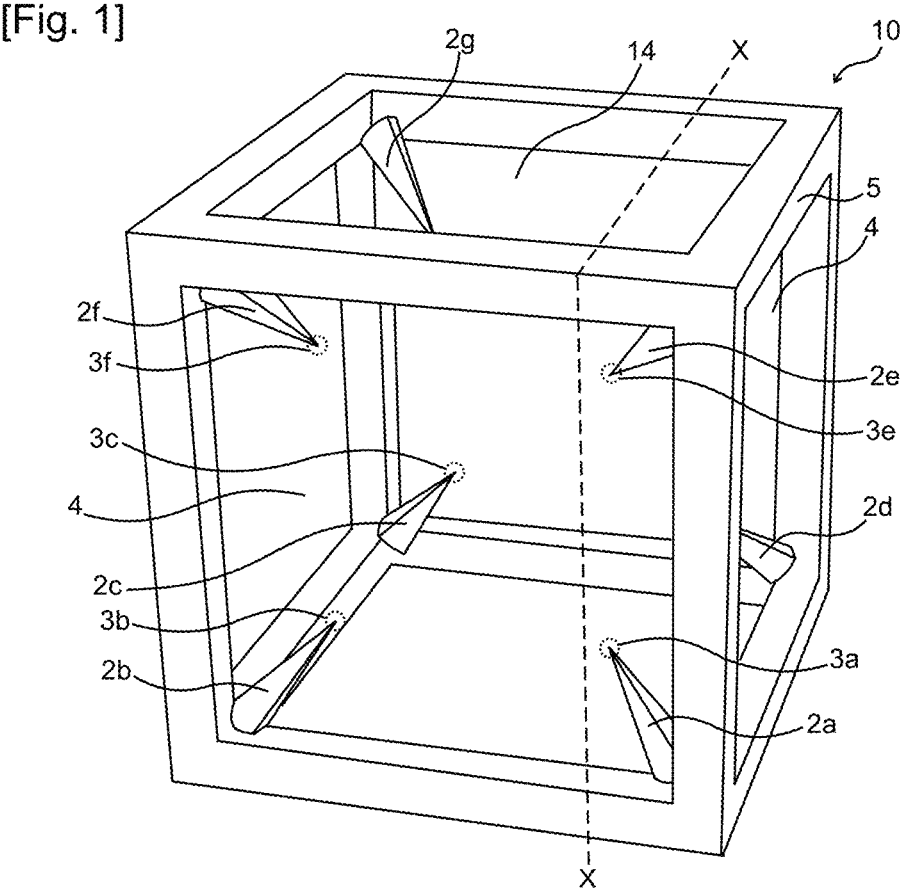
[Fig. 2]
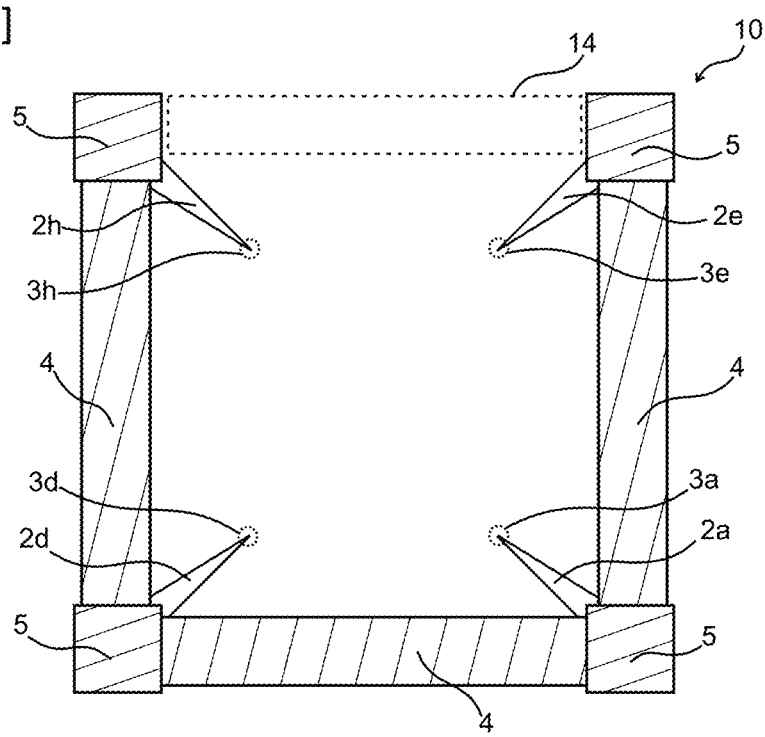

[Fig. 3]
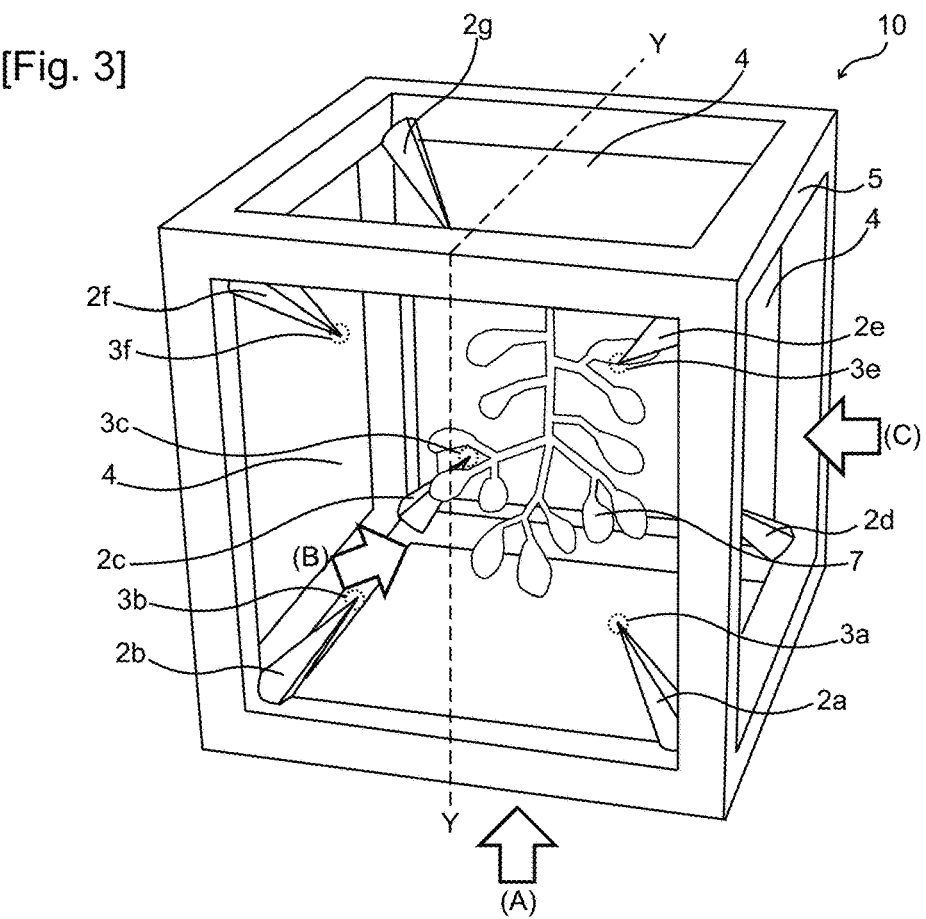
[Fig. 4]
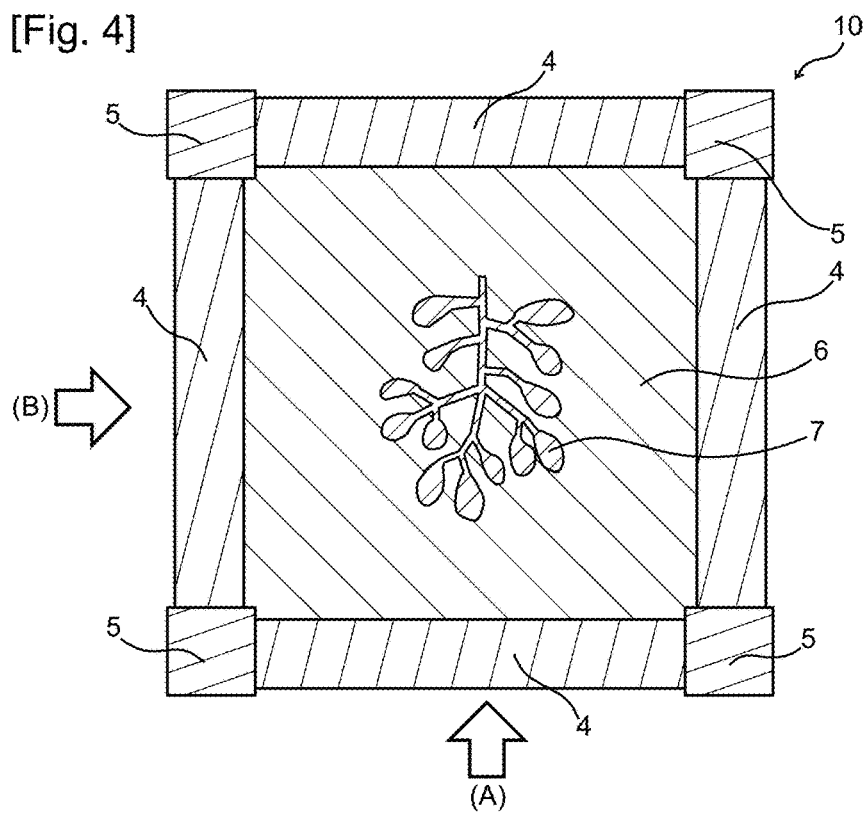

[Fig. 5]
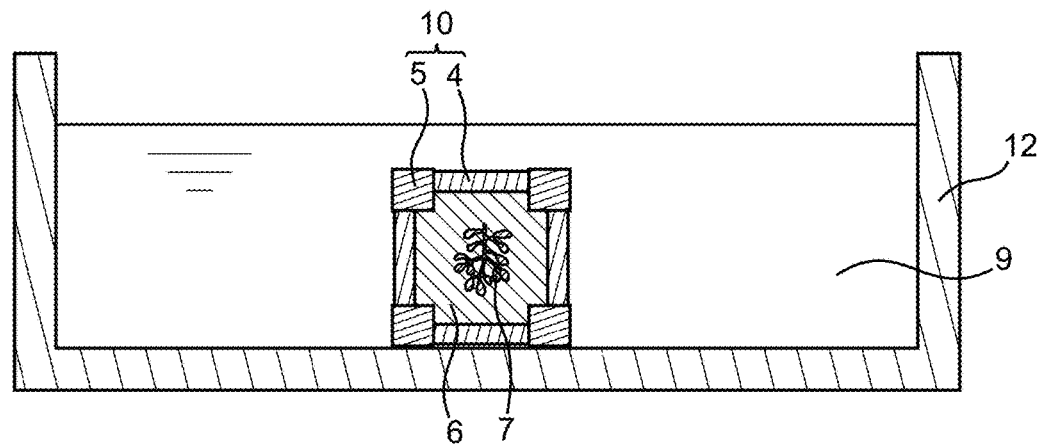
[Fig. 6]
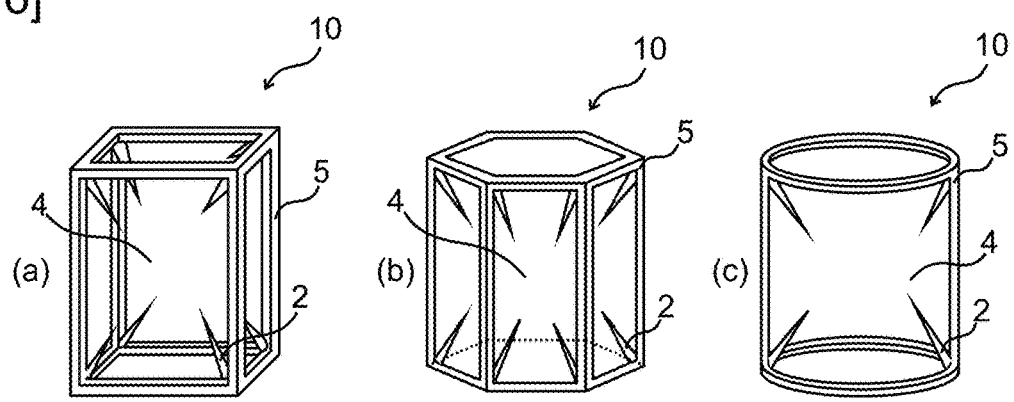

[Fig. 7]
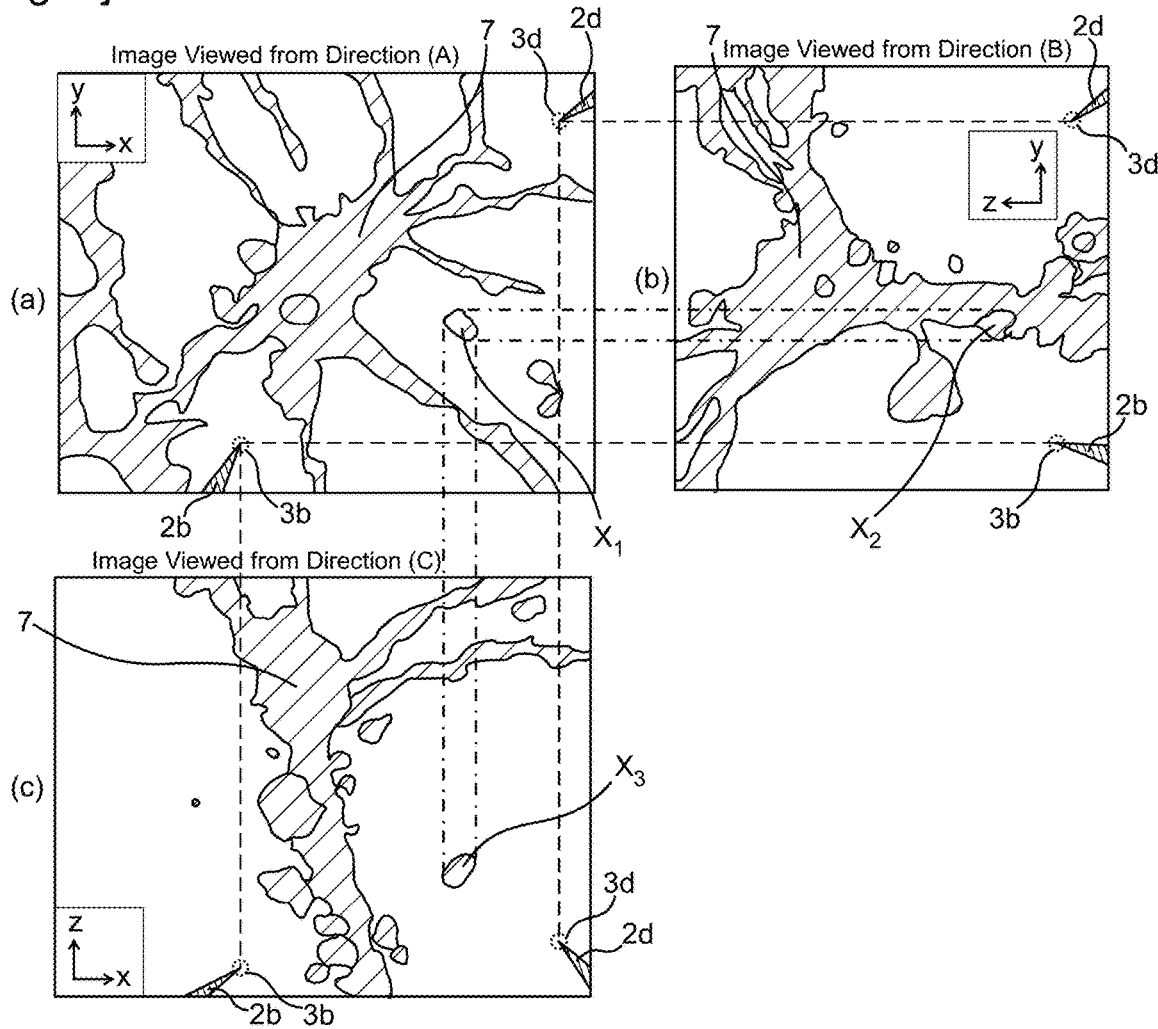
[Fig. 8]
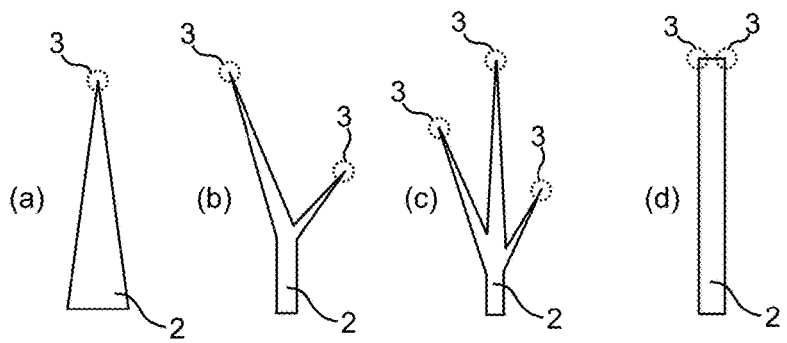

CELL CULTURE VESSEL, SAMPLE OBSERVATION CELL, AND CELL CULTURE METHOD

TECHNICAL FIELD

The present invention relates to a cell culture vessel, a sample observation cell, and a cell culture method.

BACKGROUND ART

Studies have been conducted on formation of blood vessel tissue, bronchial tissue, etc. by culturing cell tissue in three dimensions in a culture gel (see, for example, Patent Literatures 1 to 3). In these studies, a thick-layered culture gel is usually prepared in a dish or a well; and cells or cell tissue is embedded in this culture gel layer to culture the cell tissue. An observation means is to observe the cultured cell tissue from the lower side or the upper side of the culture gel layer by using an inverted microscope or an upright microscope. In PTL 3, cells stained with a dye are observed with a confocal laser microscope.

The confocal laser microscope is capable of bringing a laser beam into focus on the cells with use of an objective lens and detecting autofluorescence of labeled fluorescent material in the focused cells. This allows for a three-dimensional image of the cells by superimposing a plurality of two-dimensional images of focal planes (x-y planes) in a z direction.

CITATION LIST

Patent Literatures

[PTL 1]
Japanese Unexamined Patent Application Publication No. 2009-213716
[PTL 2]
WO 2004/084967 A
[PTL 3]
WO 2012/147878 A

SUMMARY OF INVENTION

Technical Problems

In a case where relatively-large cell tissue is observed with the confocal laser microscope, it is necessary to use a low-magnification objective lens. The low-magnification objective lens is prone to deepen a focal depth and to decrease a resolution in the z direction. This makes it difficult to obtain a clear three-dimensional image.

In a case where multifaceted observation is carried out to observe cells, the following are commonly carried out: Find cells having uniqueness that makes the cells recognized as the same thing in every image; match the observation images taken from different directions by using the cells; and perceive a three-dimensional structure of the cells. This method, however, takes time to match the observation images taken from the different directions. Furthermore, it is difficult to carry out the accurate matching. Additionally, in a case where multifaceted observation is carried out to observe relatively less distinct cells, it is difficult to match observation images taken from different directions.

The present invention is developed in view of such circumstances, and provides a cell culture vessel/sample observation cell that is capable of culturing cells or cell tissue in three dimensions and allowing a three-dimensional structure of the cells or the cell tissue to be perceived easily.

Solutions to Problems

The present invention provides a cell culture vessel for containing a culture gel in which cells or cell tissue is embedded, the cell culture vessel/sample observation cell being characterized by comprising a frame, at least one window bordered by the frame, and at least one projection projecting from the frame inwardly into the cell culture vessel/sample observation cell, wherein the at least one window is light-permeable and nutrient component-permeable and is placed in such a way as to allow for multifaceted observation of the cells or the cell tissue; and the projection has a feature point to be placed at a position where the cells or the cell tissue as well as the feature point can be observed from the window.

Advantageous Effects of Invention

The cell culture vessel/sample observation cell according to the present invention is designed to contain the culture gel in which the cells or the cell tissue is embedded. This allows the culture gel to function as a scaffold of the cells or the cell tissue and allows the cells or the cell tissue to be cultured in three dimensions in the culture gel contained in the cell culture vessel/sample observation cell.

Since the cell culture vessel/sample observation cell according to the present invention has the nutrient component-permeable window, the cell culture vessel/sample observation cell can supply nourishment, such as proteins and oxygen, in a liquid culture medium to the cells or the cell tissue through the window and the culture gel as the cell culture vessel/sample observation cell is immersed in the liquid culture medium.

Since the cell culture vessel/sample observation cell according to the present invention comprises the frame and the at least one window bordered by the frame, the cell culture vessel/sample observation cell can be strengthened, making the cell culture vessel/sample observation cell easy to handle. The frame can prevent damage to the window. Also, the frame allows the cell culture vessel/sample observation cell to rotate easily.

The above-described window is light-permeable and is placed in such a way as to enable the cells or the cell tissue to be multifacetedly observed. This makes it possible for the cells or the cell tissue inside the cell culture vessel/sample observation cell to be multifacetedly observed from the window after the vessel is set on a stage of a microscope. The cell culture vessel/sample observation cell may be rotated so that the cells or the cell tissue can be multifacetedly observed from each of faces of the cell culture vessel/sample observation cell.

The cell culture vessel/sample observation cell according to the present invention has the at least one projection projecting from the frame inwardly into the cell culture vessel/sample observation cell. This allows a tip portion of the projection to be positioned inside the cell culture vessel/sample observation cell.

The above-described projection has the feature point to be placed at a position where the cells or the cell tissue as well as the feature point can be observed from the above-described window. This makes it possible for the feature point to appear on the observation images taken from the different directions when the cells or the cell tissue is subjected to the multifaceted observation from the window.

By using this feature point as a reference point, the observation images taken from the different directions can be subjected to matching with a high degree of accuracy regardless of a shape of the cell tissue, perceiving a three-dimensional structure of the cells or the cell tissue as an observation object.

In a case where there are a plurality of windows, a plurality of observation images taken from every window can be subjected to matching. In a case where there is one window, a plurality of observation images taken from the one window but taken at different angles can be subjected to matching.

BRIEF DESCRIPTION OF DRAWINGS

FIG. 1 illustrates a diagrammatic perspective view of a cell culture vessel/sample observation cell in accordance with one embodiment of the present invention.

FIG. 2 illustrates a diagrammatic cross-section view of the cell culture vessel/sample observation cell taken along the dashed line X-X of FIG. 1.

FIG. 3 illustrates a diagrammatic perspective view of a cell culture vessel/sample observation cell in accordance with one embodiment of the present invention.

FIG. 4 illustrates a diagrammatic cross-section view of the cell culture vessel/sample observation cell taken along the dashed line Y-Y of FIG. 3.

FIG. 5 illustrates a diagrammatic cross-section view of a cell culture vessel/sample observation cell in a state of being immersed in a liquid culture medium in accordance with one embodiment of the present invention.

FIGS. 6(*a*) to 6(*c*) respectively illustrate diagrammatic perspective views of cell culture vessels/sample observation cells in accordance with one embodiment of the present invention.

FIG. 7(*a*) illustrates a diagrammatic view of an observation image of cell tissue viewed from a direction (A) indicated in FIGS. 3 and 4; FIG. 7(*b*) illustrates a diagrammatic view of an observation image of the cell tissue viewed from a direction (B) indicated in FIGS. 3 and 4; and FIG. 7(*c*) illustrates a diagrammatic view of an observation image of the cell tissue viewed from a direction (C) indicated in FIG. 3.

FIGS. 8(*a*) to 8(*d*) respectively illustrate diagrammatic views of projections included in a cell culture vessel/sample observation cell in accordance with one embodiment of the present invention.

DESCRIPTION OF EMBODIMENTS

The cell culture vessel/sample observation cell according to the present invention is configured to contain a culture gel in which cells or cell tissue is embedded, the cell culture vessel/sample observation cell being characterized by comprising a frame, at least one window bordered by the frame, and at least one projection projecting from the frame inwardly into the cell culture vessel/sample observation cell, wherein the at least one window is light-permeable and nutrient component-permeable and is placed in such a way as to allow for multifaceted observation of the cells or the cell tissue; and the projection has a feature point to be placed at a position where the cells or the cell tissue as well as the feature point can be observed from the window.

It is desirable that the at least one window should be made from a hydrogel or a porous solid; and it is desirable that the porous solid should include at least one of a porous material-made sheet, a mesh, an etching sheet, a non-woven cloth, and a woven cloth. This makes it possible for the window to have nutrient component permeability, and makes it possible to supply nutrient components to the cells or the cell tissue inside the cell culture vessel.

It is desirable that the frame of the cell culture vessel/sample observation cell according to the present invention should be shaped like a cube or a rectangular parallelepiped, and should have an opening for placing the window at each of the faces of the frame. This allows the cell tissue to be observed from an x-axis direction, a y-axis direction, and a z-axis direction of space coordinates in an interior space of the cell culture vessel, and allows a three-dimensional structure of the cell tissue to be perceived easily.

It is desirable that the cell culture vessel/sample observation cell according to the present invention should have a plurality of projections, and that each projection should have the feature point. This allows the plurality of feature points to be shown in the observation images of the cell tissue; and when the observation images taken from the different directions are matched, the plurality of feature points are used as reference points so that rotation, etc. of the observation images can be adjusted. This allows for precise matching of the observation images taken from the different directions.

It is desirable that the projection included in the cell culture vessel/sample observation cell according to the present invention should have a plurality of feature points. This allows the plurality of feature points to be shown in the observation images of the cell tissue; and when the observation images taken from the different directions are matched, the plurality of feature points are used as reference points so that rotation, etc. of the observation images can be adjusted. This allows for precise matching of the observation images taken from the different directions.

It is desirable that the projection included in the cell culture vessel/sample observation cell should be configured in such a way that at least the feature point is made of autofluorescent material. This allows the feature point to become luminous when fluorescent observation is carried out to observe the cell tissue with use of a confocal laser microscope or the like; and by using the feature point of the projection as the reference point during the fluorescent observation, fluorescent observation images taken from different directions can be accurately matched.

It is desirable that the window included in the cell culture vessel/sample observation cell according to the present invention should include an agarose gel, a polyacrylamide gel, a sodium alginate, or a collagen gel. This enables nourishment, stimulatory factors, etc. that are necessary for the cultivation of the cell tissue to pass through the window. By immersing the cell culture vessel/sample observation cell in the liquid culture medium, the nourishment, the stimulatory factors, etc. included in the liquid culture medium can be supplied to the cell tissue through the window and the culture gel. This also enables the window to have the light permeability and enables the cell tissue inside the cell culture vessel/sample observation cell to be observed though the window. Furthermore, this enables the window to have sufficient strength and prevents the window from being deformed by a weight of the culture gel placed inside the cell culture vessel/sample observation cell.

The present invention also provides a cell culture method comprising the steps of: culturing cells or cell tissue in a cell culture vessel/sample observation cell containing a culture gel in which the cells or the cell tissue is embedded; and observing the cells or the cell tissue cultured in the cell culture vessel/sample observation cell, wherein the cell culture vessel/sample observation cell is characterized by comprising at least one window, the at least one window being light-permeable and nutrient component-permeable and being placed in such a way as to allow for multifaceted observation of the cells or the cell tissue, and the method is characterized in that a reference object having a feature point is placed in the cell culture vessel/sample observation cell before the step of culturing the cells or the cell tissue is carried out, the feature point being placed at a position where the cells or the cell tissue as well as the feature point can be observed from the window.

The present invention also provides a frame designed for a cell culture vessel configured to contain a culture gel in which cells or cell tissue is embedded, wherein the frame is characterized by having at least one opening at which a window is formed and by having at least one projection projecting from the frame inwardly, wherein the window is light-permeable and also nutrient component-permeable and is placed in such a way as to allow for multifaceted observation of the cells or the cell tissue; and the projection has a feature point to be placed at a position where the cells or the cell tissue can be observed together with the feature point from the window.

In the following, one embodiment of the present invention will be described through the use of drawings. Note that compositions indicated in the drawings and the following descriptions are exemplifications and are not to limit the present invention only to the drawings and the following descriptions.

FIG. 1 illustrates a diagrammatic perspective view of a cell culture vessel/sample observation cell in accordance with the present embodiment, and FIG. 2 illustrates a diagrammatic cross-section view of the cell culture vessel/sample observation cell taken along the dashed line X-X of FIG. 1. FIG. 3 illustrates a diagrammatic perspective view of the cell culture vessel/sample observation cell of FIGS. 1 and 2 in a state of containing a culture gel in which cell tissue is embedded; and FIG. 4 illustrates a diagrammatic cross-section view of the cell culture vessel/sample observation cell taken along the dashed line Y-Y of FIG. 3.

A cell culture vessel/sample observation cell 10 in accordance with the present embodiment is to contain a culture gel 6 configured to have cells or cell tissue 7 embedded therein, and is characterized by having a frame 5, at least one window 4 bordered by the frame 5, and at least one projection 2 projecting from the frame 5 inwardly into the cell culture vessel/sample observation cell 10, wherein the at least one window 4 is light-permeable and nutrient component-permeable and is placed in such a way as to allow for multifaceted observation of the cells or cell tissue 7; and the projection 2 has a feature point 3 to be placed at a position where the cells or cell tissue 7 can be observed together with the feature point from the window 4.

In the following, the cell culture vessel/sample observation cell 10 in accordance with the present embodiment will be described.

The cell culture vessel/sample observation cell 10 of the present embodiment is a vessel that is capable of culturing the cells or cell tissue 7 by containing the culture gel 6 in which the cells or cell tissue 7 is embedded, and also is a sample cell that allows cultured cells or cell tissue 7 to be observed through the window 4. The cell culture vessel 10 is the same thing as the sample observation cell 10.

The cell culture vessel 10 in accordance with the present embodiment may be in a state in which the culture gel 6, which is configured to have the cells or cell tissue 7 embedded therein, is not contained in the cell culture vessel. In this case, the cell culture vessel 10 can have an opening 14 that is used when the culture gel 6 and the cell tissue 7 are injected into the vessel. This opening 14 can be covered (sealed) with the window 4 after the culture gel 6 and the cell tissue 7 are injected into the vessel. The opening 14 can be placed at an upper face of the cell culture vessel 10. The cell culture vessel 10 may have a structure, for example, as illustrated in FIGS. 1 and 2.

The cell culture vessel 10 in accordance with the present embodiment may be in a state in which the culture gel 6, which is configured to have the cells or cell tissue 7 embedded therein, is enclosed in the cell culture vessel. In this case, the cell culture vessel 10 may have a structure, for example, as illustrated in FIGS. 3 and 4.

The culture gel 6 to be housed in the cell culture vessel 10 is a gel that is used for culturing the cells or cell tissue 7 embedded in the culture gel 6. The cells to be embedded in the culture gel 6 may be cell tissue having a structure where cells aggregate in a specific pattern, or may be cells that do not have such a tissue structure. The cells 7 without having the tissue structure may be cultured to grow into cell tissue 7.

The cells or cell tissue 7 embedded in the culture gel 6 can be supplied with nourishment, stimulatory factors, etc. through the culture gel 6. The culture gel 6 can function as a scaffold of the cell tissue 7, and can allow the cell tissue 7 to grow in three dimensions.

The culture gel 6 can include, for example, any of collagen, laminin, entactin, and proteoglycan. The culture gel 6 can also include, for example, any of a TGF-β, a fibroblast growth factor, and a tissue plasminogen activator. Also, used for the culture gel 6 is, for example, Matrigel™.

Since the culture gel 6 is contained in the cell culture vessel 10 and is not directly in contact with a liquid culture medium 9 present outside the vessel, the culture gel 6 can be prevented from swelling by absorbing the liquid culture medium 9; and thus the cell tissue 7 is prevented from deviating from its relative position.

The cell culture vessel 10 has the frame 5 and the at least one window 4 bordered by the frame 5. This allows for an interior space formed by the frame 5 and the window 4; and the cell culture vessel 10 can house the culture gel 6 therein, which has the cells or cell tissue 7 embedded therein.

The frame 5 of the cell culture vessel 10 can strengthen the cell culture vessel 10 and makes the cell culture vessel 10 easy to handle. The frame also allows the cell culture vessel 10 to rotate easily. Moreover, the frame can prevent damage to the window 4. Furthermore, the frame 5 is configured to be three-dimensional and to have at least one opening, and is configured to have the window 4 in such a way as to cover this opening. The frame 5 is also configured to be three-dimensional and to have a plurality of openings, and is configured to have a plurality of windows 4 in such a way as to cover the plurality of openings, respectively.

The frame 5 may be made from a biocompatible resin as its material. Used as the material of the frame 5 is, for example, a polycarbonate.

The window 4 has the nutrient component permeability. This allows nourishment—such as proteins (having a molecular weight of tens of thousands to hundreds of thousands), chemical substances, and oxygen—to pass through the window 4, and makes it possible to supply the nourishment necessary for the cultivation from the liquid culture medium 9, etc. present outside the cell culture vessel 10 to the cell tissue 7 through the window 4 and the culture gel 6. The window 4 may be made from a hydrogel or a porous solid as its material.

The hydrogel is in the form of a solid formed by linking dispersoid in water and forming a network as the whole of a system. The window 4 may be adapted to have sufficient protein permeability to supply the protein to the cell tissue 7.

The porous solid is material having numerous minute pores. The porous solid may be in the form of, for example, a porous material-made sheet, a mesh, an etching sheet, a non-woven cloth, or a woven cloth. The porous solid may be in the form of a sheet. It is desirable that the porous solid should be biocompatible. The porous solid may be made of a resin such as a polycarbonate, or may be made of a metal such as gold, or may be made of an inorganic compound such as glass.

As illustrated in FIG. 5, for example, the cell culture vessel 10 may be immersed in the liquid culture medium 9 so that the nourishment, such as proteins, chemical substances, and oxygen, contained in the liquid culture medium 9 may be supplied to the cell tissue 7 through the window 4 and the culture gel 6. Or the cell culture vessel 10 may be placed in a flow passage through which the liquid culture medium 9 flows.

The window 4 has strength that the window 4 does not become significantly deformed or has strength that the window 4 is not damaged (does not break), even when the cell culture vessel 10 encloses the culture gel 6 therein.

The window 4 has light permeability. This makes it possible for the cell tissue 7 inside the cell culture vessel 10 to be observed through the window 4. The cell tissue 7 may be observed through the window 4 while the cell tissue is in the process of being cultured or after the cultivation of the cell tissue is completed. The cell tissue 7 may be stained with a dye so that fluorescent observation can be carried out to observe the cell tissue through the window 4.

The window 4 may be placed so as to cover (seal) the opening bordered by the frame 5. The window 4 may be in the form of a film or a sheet. The thinner the window 4 is, the better. This improves the protein permeability and the light permeability of the window 4.

For example, the strength and the protein permeability of the window 4 made of the hydrogel can be adjusted by adjusting a concentration of the dispersoid that forms the network of the hydrogel used for the window 4.

The higher the concentration of the dispersoid forming the network is, the higher the strength of the window 4 becomes. It is desirable that the window 4 should have the gel strength of 50 g/cm$^2$ or higher. This can prevent the window 4 from being deformed by a weight of the culture gel 6 inside the cell culture vessel 10.

An overly high concentration of the dispersoid of the window 4 causes a decrease in the protein permeability; therefore, to secure the protein permeability, it is desirable that the concentration of the dispersoid should be controlled (or adjusted) in such a way that the window 4 has the strength of 10,000 g/cm$^2$ or lower.

It is thus preferable that the window 4 should have the strength of 50 g/cm$^2$ or higher to 10,000 g/cm$^2$ or lower. An adequate concentration of the dispersoid in order to obtain the gel strength such as the one above varies depending on a kind of the dispersoid.

The window 4 may include, for example, an agarose gel, a polyacrylamide gel, a sodium alginate, or a collagen gel. This allows the window 4 to have the light permeability. In the case where the cell culture vessel 10 is immersed in the liquid culture medium 9, the nourishment, such as the proteins, contained in the liquid culture medium 9 passes through the window 4; and this allows the nourishment to be supplied to the cell tissue 7 through the window 4 and the culture gel 6. Since the window 4 includes the agarose gel, the polyacrylamide gel, the sodium alginate, or the collagen gel, the window 4 can be prevented from being deformed while the cell culture vessel 10 is rotated. It is preferable that the window 4 should be made from the agarose gel or the polyacrylamide gel. This makes it easy to adjust hardness of the window 4. This can also reduce production costs of the cell culture vessel 10.

In the case where the window 4 is made of the agarose gel, a concentration of agarose may be, for example, 0.5 to 4.0%. In the case where the window 4 is made of the polyacrylamide gel, a concentration of polyacrylamide may be, for example, 3 to 20%. To form the sodium alginate-containing window 4, calcium ions are added to a sodium alginate solution so as to gelatinize the solution. To form the collagen gel-containing window 4, the collagen gel should be high in concentration. This makes it possible for the window 4 to have adequate strength.

A shape of the cell culture vessel 10 is not particularly limited, as long as the cell culture vessel has the interior space adapted to contain the culture gel 6 in which the cells or cell tissue 7 is embedded; and the cell culture vessel may have a cubic shape as illustrated in FIGS. 1 to 4, or may be shaped like a rectangular parallelepiped as illustrated in FIG. 6(*a*), or may be shaped like a hexagonal column as illustrated in FIG. 6(*b*). The cell culture vessel 10 may also be shaped like a circular cylinder as illustrated in FIG. 6(*c*). It is, however, preferable that the cell culture vessel 10 should be shaped like a cube or a rectangular parallelepiped. This allows the cell tissue 7 to be observed from an x-axis direction, a y-axis direction, and a z-axis direction of space coordinates in the interior space of the cell culture vessel 10, and allows a three-dimensional structure of the cell tissue 7 to be perceived easily.

In the case where the cell culture vessel 10 is polyhedral in shape as illustrated in FIGS. 1 to 4, 6(*a*) and 6(*b*), the frame 5 can be in the form of a polyhedron, enabling the polyhedral cell culture vessel to have openings at its every face so that windows 4 can be respectively formed at the openings. In the case where the cell culture vessel 10 is shaped like the circular cylinder as illustrated in FIG. 6(*c*), the frame can be in the form of a cylinder, enabling the cylindrical cell culture vessel to have openings at its upper face, lower face, and side face, respectively, so that windows 4 can be respectively formed at the openings.

To form a hydrogel-containing window 4, a sol for window is poured through the opening bordered by the frame 5 and is gelatinized. The window 4 may be flat or curved. By making the window 4 curved, the cell tissue 7 can be multifacetedly observed from the only one window 4.

Before the culture gel 6 is placed in the cell culture vessel 10, windows 4 may be formed at the openings except the opening 14 at the upper face of the frame 5. After the culture gel 6 and the cell tissue 7 are placed inside the cell culture vessel 10 through the opening 14 at the upper face of the frame 5, a window 4 may be formed at the opening 14 at the upper face of the frame 5.

When using the porous solid to form a window 4, the porous solid in the form of a sheet may be pasted to the frame 5 so as to form the window 4.

By forming the windows 4 at the openings of the three-dimensional frame 5 as illustrated in FIGS. 1 to 4 and 6, the cell tissue 7 placed inside the cell culture vessel 10 can be observed from different directions, allowing for multifaceted observation of the cell tissue 7.

By being polyhedral, the cell culture vessel 10 can be rotated in such a way as to enable the cell tissue 7 to be observed from every face of the polyhedron so that a microscope can take observation images of the cell tissue 7 from the different faces of the cell culture vessel.

The cell culture vessel 10 has at least one projection 2 protruding from the frame 5 inward into the cell culture vessel 10. This allows a tip portion of the projection 2 to be positioned inside the cell culture vessel 10. The projection 2 may be made of the same material as the frame 5. To serve as the projection 2, a material object may be pasted to the frame 5.

The projection 2 may be placed so as to project from the frame 5 toward a central portion of the vessel. By being placed in this way, the projection 2 is unlikely to impede the growth of the cell tissue 7. The exemplary illustrations of FIGS. 1, 2 and 6 show the projections 2 protruding inwardly only from joints (folds) of the frame 5. Namely, the polyhedral cell culture vessel 10 has the projections 2 that are placed inside of corners (or at valley folds) of the frame 5. Particularly in this case, the projections 2 are placed at positions distant from the central portion of the vessel and thus do not get in the way of the growth of the cell tissue 7.

The projection 2 has the feature point 3 to be placed at a position where the cells or cell tissue 7 together with the feature point can be observed from the window 4. This enables the feature point 3 to appear on the observation images taken from the different directions when the cells or cell tissue 7 is multifacetedly observed from the window 4. By using this feature point 3 as a reference point, the observation images taken from the different directions can be accurately matched, with the result that the three-dimensional structure of the cells or cell tissue 7 as an observation object can be perceived.

The exemplary illustrations of FIGS. 1 to 3 show projections 2a to 2f protruding inward from the corners of the frame 5 toward the inner side of the vessel, enabling one projection 2 placed at the corner to be observed from three windows 4 adjoining the corner. The images thereby observed from these three windows 4 thus can be subjected to precise matching.

The exemplary illustrations of FIGS. 1 to 3 and 6 show a shape of the projections 2 such that the projections taper off to a pointed tip, and this tip portion serves as the feature point 3, enabling light to pass around the feature point 3. Namely, the projection 2 is designed in such a way that its feature point 3 can be easily observed from the different directions.

The shape of the projection 2, however, is not limited to those illustrated in the drawings; and the projection 2 may be configured to have a shape such as being angulated (polyhedron, etc.); and a tip thereof may be used as the feature point 3. The projection 2 may have, for example, a spherical portion; and a center or a tip of the spherical portion may serve as the feature point 3.

FIG. 7(a) illustrates a diagrammatic view of an observation image of cell tissue 7 viewed from a direction (A) indicated in FIGS. 3 and 4; FIG. 7(b) illustrates a diagrammatic view of an observation image of the cell tissue 7 viewed from a direction (B) indicated in FIGS. 3 and 4; and FIG. 7(c) illustrates a diagrammatic view of an observation image of the cell tissue 7 viewed from a direction (C) indicated in FIG. 3. This makes it possible to show a feature point 3b of a projection 2b and a feature point 3d of a projection 2d on the observation images viewed from the different directions. By using these feature points 3b and 3d as reference points, the images of FIGS. 7(a), 7(b) and 7(c) can be subjected to precise matching. This makes it possible to specify that cell tissue $X_1$ in the image of FIG. 7(a) and cell tissue $X_2$ in the image of FIG. 7(b) and cell tissue $X_3$ in the image of FIG. 7(c) indicate the same cell tissue, obtaining an accurate view of a three-dimensional structure of this cell tissue.

The cell culture vessel 10 may have a plurality of projections 2. This makes it possible to show a plurality of feature points 3 in observation images of cell tissue 7; and the observation images taken from different directions can be subjected to positioning by using the plurality of feature points 3 as reference points, with the result that rotation, etc. of the observation images can be adjusted. This allows for precise positioning of the observation images taken from the different directions. For example, the cell culture vessel 10 illustrated in FIGS. 1 to 4 has eight (8) projections 2a to 2h. As illustrated in FIGS. 6(a) to 6(c), a plurality of projections 2 may be placed in the cell culture vessels 10.

The plurality of projections 2 may be configured to have lengths different from each other and projection angles different from each other. This enables the feature points 3 to be arranged at various positions inside the cell culture vessel 10, and the suitable feature points 3 can be chosen according to cell tissue 7 to be observed. For example, in a case where cell tissue 7 to be observed spreads widely, optimal feature points 3 can be chosen section by section as reference points from the plurality of feature points 3 placed inside the cell culture vessel 10.

The plurality of projections 2 may have different shapes from each other. This makes it easy to specify the projections 2 shown in the observation images of the cell tissue 7.

A single projection 2 may have a plurality of feature points 3. In this case, a plurality of reference points can be shown in the observation images of the cell tissue 7 only by placing the single projection 2 having the plurality of feature points 3; therefore, rotation, etc. of the observation images can be modified in accordance with the plurality of reference points. This enables the observation images taken from the different directions to be subjected to more accurate positioning. The single projection 2 may have one feature point 3 as illustrated in FIG. 8(a) as an example, or may have a plurality of feature points 3 as illustrated in FIGS. 8(b) to 8(d) as examples.

The projection 2 may be made of biocompatible material. This can prevent the projection 2 from getting involved with any biological effect on the cell tissue 7. The material of the projection 2 may be biocompatible macromolecules such as a biocompatible epoxy resin or a biocompatible acrylic resin.

The projection 2 may be configured in such a way that at least the feature point 3 is made of autofluorescent material. This allows the feature point 3 to become luminous when fluorescent observation is carried out to observe the cell tissue 7 with use of a confocal laser microscope or the like. The autofluorescent material may be used for the projection 2 itself or may be used for only a portion of the feature point 3. The feature point 3 of the projection 2, which is made from the autofluorescent material, may also be used for bright field observation of the cell tissue 7.

The projection 2 may be formed, for example, by preparing a triangle plate made of a biocompatible photoresist (such as SU-8) and pasting this plate on the frame 5. The photoresist and an adhesive used to paste the projection on the frame 5 may be made from any biocompatible material.

The projection 2 may be configured in such a way that its shape can be modified. Modifying the shape of the projection 2 allows the feature point 3 thereof to change its position, enabling the position of the feature point 3 to be changed in accordance with a kind of the cell tissue 7 to be cultured in the cell culture vessel 10.

Cell Culture Method

A cell culture method in accordance with the present embodiment comprises the steps of: culturing cells or cell tissue 7 in a cell culture vessel 10 containing a culture gel 6 in which the cells or cell tissue 7 is embedded; and observing the cells or cell tissue 7 cultured in the cell culture vessel 10.

In the cell culture method in accordance with the present embodiment, a reference object 2 having a feature point 3 is placed in the cell culture vessel 10 before the step of culturing the cells or cell tissue 7 is carried out, the feature point being placed at a position where the cells or cell tissue 7 as well as the feature point can be observed from a window 4.

The reference object 2 may be referred to as the above-described projection 2.

Or the reference object 2 may be a tiny object (a minute object) embedded in the culture gel 6. The reference object 2 may be embedded in the culture gel 6 before or after the cell tissue 7 is embedded in the culture gel 6. The reference object 2 is placed at a position where the reference object together with the cell tissue 7 can be observed from the window 4, and is placed at a position where does not impede the growth of the cell tissue 7. The feature point 3 of such a reference object 2 can be used as a reference point so that observation images taken from different directions can be accurately matched, obtaining an accurate view of a three-dimensional structure of the cells or cell tissue 7 as an observation object.

A plurality of reference objects 2 may be embedded in the culture gel 6. Or a reference object 2 having a plurality of feature points 3 may be embedded in the culture gel 6.

The reference object 2 may be shaped like, for example, a cube, a star, a tetrahedron, or a sphere.

In the culturing step, cells or cell tissue 7 can be cultured by, for example, immersing a cell culture vessel 10 in a liquid culture medium 9 stored in a culture dish 12 or by placing a cell culture vessel 10 in a flow passage through which a liquid culture medium 9 flows.

In the observing step, the cell culture vessel 10 (sample observation cell 10) is taken out of the liquid culture medium 9 and is set on a stage of a microscope so that the cells or cell tissue 7 can be observed. The cell tissue 7 can be observed by bright field observation or fluorescent observation. For the fluorescent observation, the cell tissue 7 in the cell culture vessel 10 is stained with a dye, and then the fluorescent observation is carried out.

In the case where the cell culture vessel 10 is polyhedral as illustrated in FIGS. 1 to 4, 6(*a*) and 6(*b*), the cell culture vessel 10 (sample observation cell 10) can be rotated in such a way as to enable the cell tissue 7 to be observed from different faces of the polyhedron, allowing the cell tissue 7 to be multifacetedly observed.

The cell tissue 7 may be observed after the cell culture vessel 10 (sample observation cell 10) is placed in a glass container. This prevents the liquid culture medium 9 from adhering to the microscope.

REFERENCE SIGNS LIST 2, 2*a*, 2*b*, 2*c*, 2*d*, 2*e*, 2*f*, 2*g*, 2*h*: Projection (reference object)
3, 3*a*, 3*b*, 3*c*, 3*d*, 3*e*, 3*f*, 3*g*, 3*h*: Feature point
4: Window
5: Frame
6: Culture gel
7: Cells or cell tissue
9: Liquid culture medium
10: Cell culture vessel or sample observation cell
12: Culture dish
14: Opening

The invention claimed is:

1. A cell culture vessel for containing a culture gel in which cells or cell tissue is embedded, the cell culture vessel comprising a frame, at least one window bordered by the frame, and at least one projection projecting from the frame inwardly into the cell culture vessel, wherein the at least one window is light-permeable and nutrient component-permeable and is placed in such a way as to allow for multifaceted observation of the cells or the cell tissue, and the projection has a feature point to be placed at a position where the cells or the cell tissue as well as the feature point can be observed from the window, the feature point being used as a reference point in a matching of observation images taken from different directions in the multifaceted observation of the cells or the cell tissue.

2. The cell culture vessel according to claim 1, wherein the at least one window is made from a hydrogel or a porous solid, and the porous solid includes at least one of a porous material-made sheet, a mesh, an etching sheet, a non-woven cloth, and a woven cloth.

3. The cell culture vessel according to claim 1, wherein the frame is shaped like a cube or a rectangular parallelepiped, and has an opening for placing the window at each of faces of the frame.

4. The cell culture vessel according to claim 1, wherein the cell culture vessel has projections including the at least one projection, and each of the projections has a respective feature point.

5. The cell culture vessel according to claim 1, wherein the projection has feature points including the feature point.

6. The cell culture vessel according to claim 1, wherein the projection has a taper-shaped portion at a tip thereof.

7. The cell culture vessel according to claim 1, wherein the cell culture vessel has at least two windows including the at least one window, and the projection has the feature point to be placed at a position where the feature point can be observed from the at least two windows.

8. The cell culture vessel according to claim 1, wherein the projection is configured in such a way that at least the feature point is made of autofluorescent material.

9. The cell culture vessel according to claim 1, wherein the window includes an agarose gel, a polyacrylamide gel, a sodium alginate, or a collagen gel.

10. A sample observation cell for containing a culture gel in which cells or cell tissue is embedded, the sample observation cell comprising a frame, at least one window bordered by the frame, and at least one projection projecting from the frame inwardly into the sample observation cell, wherein the at least one window is light-permeable and nutrient component-permeable and is placed in such a way as to allow for multifaceted observation of the cells or the cell tissue, and the projection has a feature point to be placed at a position where the cells or the cell tissue as well as the feature point can be observed from the window, the feature point being used as a reference point in a matching of observation images taken from different directions in the multifaceted observation of the cells or the cell tissue.

* * * * *